(12) United States Patent
Rubenstein

(10) Patent No.: US 11,215,596 B2
(45) Date of Patent: Jan. 4, 2022

(54) FOCUSING AGENTS AND METHODS OF USING SAME

(71) Applicant: Government of the United States as Represented by the Secretary of the Air Force, Wright-Patterson AFB, OH (US)

(72) Inventor: H. Mitchell Rubenstein, Beavercreek, OH (US)

(73) Assignee: United States of America as represented by the Secretary of the Air Force, Wright-Patterson AFB, OH (US)

( * ) Notice: Subject to any disclaimer, the term of this patent is extended or adjusted under 35 U.S.C. 154(b) by 254 days.

(21) Appl. No.: 16/415,118

(22) Filed: May 17, 2019

(65) Prior Publication Data
US 2020/0292513 A1    Sep. 17, 2020

Related U.S. Application Data

(62) Division of application No. 15/451,438, filed on Mar. 7, 2017.

(Continued)

(51) Int. Cl.
| | | |
|---|---|---|
| G01N 33/00 | (2006.01) | |
| G01N 30/08 | (2006.01) | |
| G01N 30/72 | (2006.01) | |
| G01N 30/86 | (2006.01) | |
| G01N 1/40 | (2006.01) | |
| B01D 53/02 | (2006.01) | |
| G01N 30/02 | (2006.01) | |

(52) U.S. Cl.
CPC ....... *G01N 33/0057* (2013.01); *B01D 53/025* (2013.01); *G01N 1/405* (2013.01); *G01N 30/08* (2013.01); *G01N 30/7206* (2013.01); *G01N 30/8668* (2013.01); *G01N 33/0006* (2013.01); *G01N 2030/025* (2013.01); *G01N 2030/085* (2013.01)

(58) Field of Classification Search
CPC ............... G01N 33/0057; G01N 1/405; G01N 33/0006; B01D 53/025
See application file for complete search history.

(56) References Cited

U.S. PATENT DOCUMENTS

| | | | | |
|---|---|---|---|---|
| 2006/0094118 A1* | 5/2006 | Tipler | ................... | G01N 30/06 436/43 |
| 2016/0203963 A1* | 7/2016 | Green | ................... | G01N 30/86 702/23 |

OTHER PUBLICATIONS

Acute Environmental Toxicity and Persistence of DEM, a Chemical Agent Simulant: Diethyl Malonate Dominic A. Cataldo, Michael W. Ligotke, Scott D. Harvey, Robert J. Fellows, Shu-mei W. Li, Peter Van Voris, Randall S. Wentsel May 1, 1990 (Year: 1990).*

(Continued)

*Primary Examiner* — Brian R Gordon
*Assistant Examiner* — Dwan A Gerido
(74) *Attorney, Agent, or Firm* — AFMCLO/JAZ; Chastity D. S. Whitaker

(57) ABSTRACT

A method for reducing the variability, as measured by relative standard deviation (RSD), of an analytical testing technique is provided. This improvement in RSD improves the confidence in the values obtained during field testing. The method includes incorporating a focusing agent into the sampling media, which permits providing sampling media such as thermal desorption tubes preloaded with the focusing agent.

9 Claims, 7 Drawing Sheets

Related U.S. Application Data

(60) Provisional application No. 62/305,395, filed on Mar. 8, 2016.

(56) References Cited

OTHER PUBLICATIONS

United States Patent and Trademark Office, Non-Final Office Action in U.S. Appl. No. 15/451,438, dated Sep. 3, 2020, 11 pages total.
United States Patent and Trademark Office, Non-Final Office Action in U.S. Appl. No. 15/451,438, dated Mar. 17, 2021, 12 pages total.

* cited by examiner

FOCUSING AGENTS AND METHODS OF USING SAME

RELATED APPLICATION

The present application is a divisional application of co-pending U.S. application Ser. No. 15/451,438, filed Mar. 7, 2017, which claims priority to U.S. Provisional Patent Application Ser. No. 62/305,395 filed Mar. 8, 2016. The disclosure of each of these applications is hereby incorporated herein by reference in its entirety.

RIGHTS OF THE GOVERNMENT

The invention described herein may be manufactured and used by or for the Government of the United States for all governmental purposes without the payment of any royalty.

FIELD OF THE INVENTION

The invention is related to improved analytical techniques useful for the identification and enhanced quantification of chemical species, such as chemical warfare agents.

BACKGROUND OF THE INVENTION

The detection and quantification of chemical warfare agents (CWAs) and toxic industrial chemicals/materials (TIC/TIM) require field analysis reliance on previously established calibration curves programmed on field instruments. Sampling tubes constructed with adsorbent materials (which are better known as thermal desorption tubes (TD)) are currently employed for field investigations, and the measured values of the CWAs, TICs, and TIMs demonstrate wide variability when control studies measure relative standard deviation (RSD).

Accordingly, disconnects exist between current field collection of samples and final analysis, and yield data that has high variability and therefor lower reliability. For example, current studies employing an exemplary portable gas chromatograph-mass spectrometer (GC/MS) HAPSITE® ER (Inficon GMBH) demonstrate wide variability of data. This variability is observed both for intra-instrumental and inter-instrumental analyses. Current experiments have demonstrated relative standard deviations (RSD) of about 70%, where the industry standard is generally about 30% RSD or less. This elevated uncertainty is especially surprising considering that the device houses a canister of an internal standard (i.e., bromopentafluorobenzene) that is capable of being injected on each sample analysis. Similar variability has been observed with comparable devices from other manufacturers.

Accordingly, there is a need for new testing protocols and equipment to enhance the reliability of these field measurements.

SUMMARY OF THE INVENTION

The present invention is premised on the realization that incorporation of an internal standard (hereinafter referred to as a "focusing agent") into an analytical sampling device by embedding a known quantity of the focusing agent onto a media component of the analytical sampling device can be leveraged to improve and enhance the reliability of analytical testing methods for quantifying chemical compound(s) of interest. More particularly, the present invention is premised on the realization that relative retention time (RRT) ratios and relative response factor (RRF) between the focusing agent and the chemical compound(s) of interest may be correlated to improve a relative standard deviation in the analytical testing method.

In accordance with an embodiment of the present invention, a system for identifying and quantifying a chemical agent is provided. The system comprises an analytical sampling device operably connected to a chromatographic subsystem and a mass spectrometer subsystem. The analytical sampling device comprises an adsorbent material, and a known quantity of a focusing agent adsorbed therein, wherein the focusing agent is characterized as having a chromatographic or spectral similarity to the chemical agent being quantified.

In accordance with another embodiment of the present invention, a method for reducing a relative standard deviation (RSD) in an analytical chromatographical testing procedure for quantifying a chemical agent is provided. The method comprises obtaining an analysis sample with an analytical sampling device to pre-concentrate the chemical agent from a fluid test sample. The analytical sampling device comprises an adsorbent material, and a known quantity of a focusing agent adsorbed therein, wherein the focusing agent is characterized as having a chromatographic or spectral similarity to the chemical agent being quantified. The method further comprises desorbing the focusing agent and the chemical agent from the analytical sampling device to form a desorbed mixture and transferring the desorbed mixture into a chromatographic subsystem and a mass spectrometer subsystem; applying the analytical chromatographical testing procedure to the test sample to obtain a first signal relating to the focusing agent and a second signal relating to the chemical agent; and correcting the first signal relating to the focusing agent and the second signal relating to the chemical agent based on a predetermined relative retention time ratio and a relative response factor between same.

The objects and advantages of the present invention will be further appreciated in light of the following detailed description and examples.

BRIEF DESCRIPTION OF THE DRAWINGS

The accompanying drawing, which are incorporated in and constitute a part of this specification, illustrate embodiments of the invention and, together with a general description of the invention given above, and the detailed description given below, serve to explain the invention. It will be appreciated that for purposes of clarity and where deemed appropriate, reference numerals have been repeated in the figures to indicate corresponding features.

DETAILED DESCRIPTION OF THE INVENTION

Figure 1:
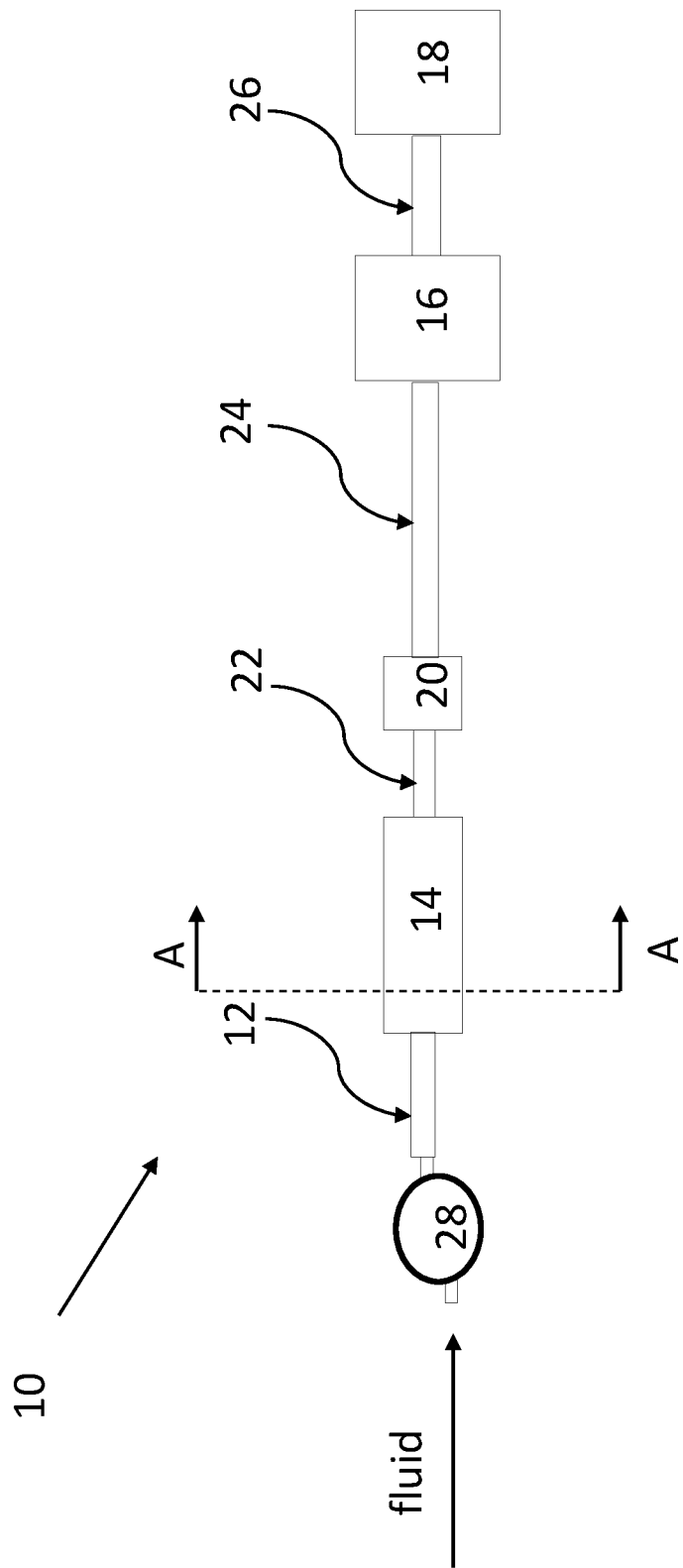
FIG. 1 is a simplified schematic of a system for identifying and quantifying a chemical agent, in accordance with an embodiment of the present invention.

With reference to FIG. 1, a simplified schematic of a system 10 for identifying and quantifying a chemical agent is shown. The system 10 includes an inlet 12 fluidly coupled to an analytical sampling device 14 operably connected to chromatographic subsystem 16 and a mass spectrometer subsystem 18. Optionally, a pre-concentrator 20 may be positioned in between the analytical sampling device 14 and the chromatographic mass spectrometer subsystems 16, 18. A pump 28 may be used to transfer a fluid sample comprising the chemical agent into contact with the analytical sampling device 14. Conduits 12, 22, 24, 26 provide fluid connections between the components of the system 10.

Figure 2:
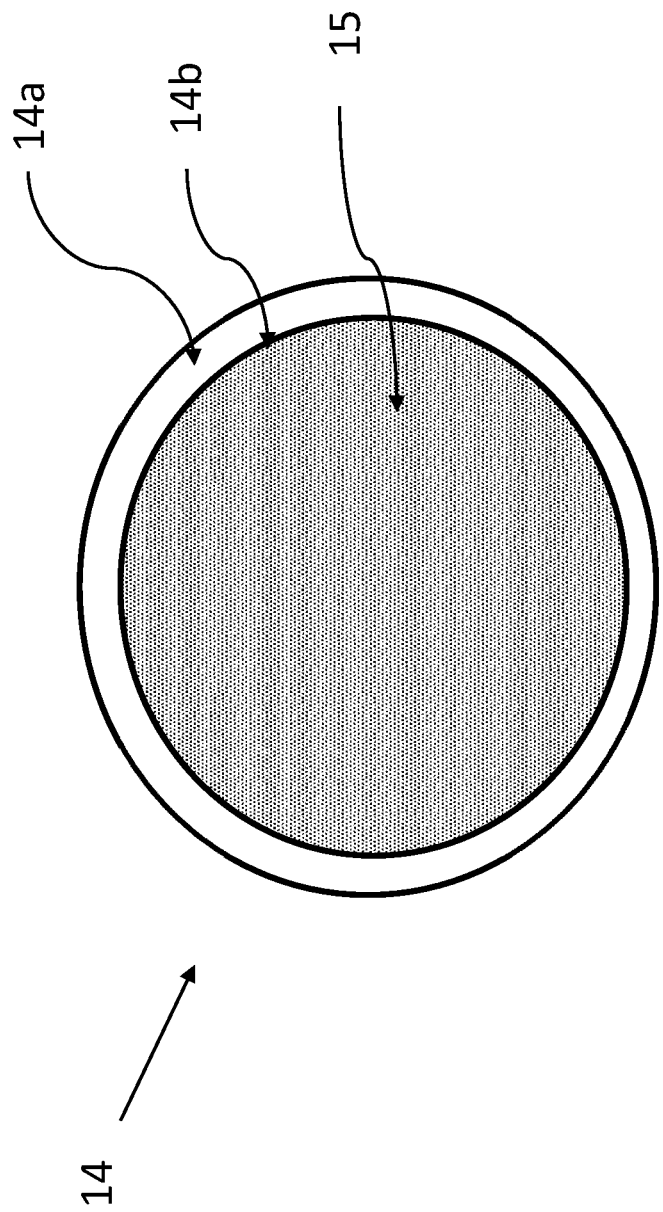
FIG. 2 is cross-sectional view of an analytical sampling device taken along line A-A of the system shown in FIG. 1.

With reference to FIG. 2, a cross-sectional view of the analytical sampling device 14 is shown, where an outer structure 14a having an inner surface 14a contains an adsorbent media or material, into which is adsorbed a focusing agent to form an embedded focusing agent region 15.

The embedding of focusing agents into the thermal desorption media tubes (or other media) advances the technology of analytical field measurements. To date multiple media has been employed to capture a variety of analytes. In accordance with embodiments described herein, we further examined stability of the exemplary embedded focusing agents, as well at the variability of the analytical chromatographical testing method, utilizing the HAPSITE® ER (INFICON GMBH). However, the embodiments and the inventive principles described herein relate to thermal desorption techniques from all manufacturers. Furthermore, the incorporation of FA may be applicable to all adsorbent media types and to other analytical techniques.

As used herein, "HAPSITE® ER" is a person-portable gas chromatograph/mass spectrometer (GC/MS) that has the capability to identify and quantify volatile organic compounds (VOCs), TICs/TIMs, CWAs, and select semi-volatile organic compounds (SVOCs).

As used herein, "adsoprtion" is a technique that concentrates volatile and semi-volatile organic compounds onto select media, while "thermal desorption" describes the liberation of volatile and semi-volatile organic compounds.

As used herein, "internal standard" is a chemical compound purposely added to samples and/or standards at a known concentration to provide a basis for comparison in quantitation.

As used herein, "simulant" includes compounds that simulate the chemistry and reactivity of chemical warfare agents (CWAs) that have considerably lower toxicity.

As used herein, "isotope dilution" means a method that improves quantitation of known compounds by the addition of known amounts of isotopically enriched substance(s) to the analyzed sample.

As used herein, "focusing agent" refers to compound(s) added to thermal desorption tubes or other media to form the analytical sampling device of the present invention and help to correlate data acquired in the absence of instrument calibration.

As used herein, "volatiles" refers to organic compounds that have a vapor pressure of 0.01 kPa or more at 20° C.

As used herein, "semi-volatiles" refers to organic compounds that have a vapor pressure less than 0.01 kPa.

As used herein, "predetermined relative retention time ratio" or "predetermined RRT ratio" refers to a ratio of the retention times (RT) for the analyte (A) with respect to the focusing agent (FA) using the analytical chromatographical testing procedure. More specifically, $RRT=RT_A/RT_{FA}$.

As used herein, "relative response factor" or "RRF" refers to a ratio between a signal produced by the analyte on a detector associated with the analytical chromatographic testing procedure, and the quantity of analyte which produces that signal, as compared to a signal produced by the focusing agent (FA), and the quantity of the FA which produces that signal. More specifically, RRF is a ratio of a (Response factor of analyte)/(Response factor of standard).

Generally speaking, portable GC/MS (such as the HAPSITE® ER) has a limitation to compounds having a boiling point (BP) less than about 280° C.

As used herein, "LOD/LOQ" refers to "limit of detection" (LOD) and "limit of quantification" (LOQ). The LOD is generally defined as 3*standard deviation (SD) of the blank, and at the LOQ is defined as 10*SD of the blank. For a signal at the LOD, the alpha error (probability of false positive) is small (1%). However, the beta error (probability of a false negative) is 50% for a sample that has a concentration at the LOD (3*SD). This means a sample could contain an impurity at the LOD, but there is a 50% chance that a measurement would give a result less than the LOD. At the LOQ (10*SD), there is minimal chance of a false negative.

Embodiments of this invention incorporate compounds of known or established concentration onto the adsorbent media of the analytical sampling device, such as a thermal desorption tubes comprising a sorbent. While the present studies concentrated on thermal desorption using Tenax®-TA resin, this technique can be extended to a wide variety of media currently employed by industry. Typical types of adsorbent materials include, but are not limited to, alumina, silica, carbon-containing adsorbents, a zeolite, a porous glass, a clay, a porous polymer based on 2,6-diphenyl-p-phenylene oxide, a hydrophobic copolymer of styrene-divinylbenzene resin, a polyurethane, or a combination thereof. More specifically, adsorbent materials of principal interest include alumina, Florisil® or other silicas, any of cyanopropyl, diol, porous glassy carbon, or Hypersil®-ODS, all available from Keystone Scientific, Bellefonte, Pa., Tenax®-TA available from Enka Research Institute of Holland, polyurethane foam, diatomaceous earth and zeolites. As will be appreciated by those of skill in the art, the choice of the adsorbent material depends on the nature of the Focusing Agent (FA) and the analyte(s) (i.e., the chemical compound(s) of interest), as well as the ability of the analytical chromatographical testing procedure to liberate the adsorbed FA and analyte(s) from the adsorbent media.

For example, silica gel tubes, Anasorb® sorbent tubes, charcoal sorbent tubes, Tenax® sorbent tubes, XAD® sorbent tubes, Chromosorb® sorbent tubes, polyurethane foam (PUF) tubes, Porapak™ sorbent tubes, OSHA Versatile Sampler (OVS) sorbent tubes, or other sorbent tubes including alumina, carbon beads, drying tubes, firebrick, florisil, glass beads, molecular sieve and soda lime tubes are known or commercially-available.

In one example, the thermal desorption tubes comprise Tenax™ TA, which has been stabilized for both sample volume collected and elevated temperatures that would be anticipated in U.S. military global surveillance. The adsorbent media can then be used to normalize data from sample to sample collected and analyzed. The experiments performed in accordance with embodiments of the present invention, show significant improvement in the quality of the data as measured by relative standard deviation (RSD).

Focusing agents are chosen based on their chromatographic similarity or spectral similarity to the chemical agent(s) under investigation. As used herein, "chromatographic similarity" is based on the selected analytical method for testing. For example, in one example, the analytical testing method is GC/MS, which is therefore associated with chromatographic similarity using a gas chromatography instrument. In another embodiment, the analytical testing method is LC/MS, which is therefore associated with chromatographic similarity using a liquid chromatography instrument. It is preferable that the Resolution ($R_s$) is sufficient to minimize interference between the signals of the FA and any analytes. $R_s=2(t_{RB}-t_{RA})/(w_B+w_A)$, where: $t_{RB}$=retention time of solute B; $t_{RA}$=retention time of solute A; $w_B$=Gaussian curve width of solute B; and $w_A$=Gaussian curve width of solute A. Chromatographically, the only critical factor is that the compounds (i.e., the focusing agent(s) and the chemical agent(s)) elute under the same chromatographic analysis conditions. Therefore, for gas chromatographical subsystems, lower boiling compounds will require lower boiling FAs and higher boiling compounds will require mid to high boiling FAs. In accordance with an embodiment of the present invention, sufficient resolution of two chromatographically similar compounds is achieved by no overlap greater than at full width half max.

As used herein, "spectral similarity" is based on the selected analytical method. Mass spectrometry is an analytical technique that ionizes chemical species and sorts the ions based on their mass-to-charge ratio. The mass spectrum of analytes is highly dependent on the structure of the molecule. Hence, one observes similar fragmentation from related compounds. An example is benzene, toluene and ethyl benzene fragment similarly and only differ by the increase in mass from the $CH_2$ groups (i.e., benzene=MW 78, toluene=92 and ethyl benzene=106). Accordingly, this attribute can be used for quantification using response factors ($R_f$), in that the compounds by mass spectral determination will provide similar $R_f$'s. Thus, in accordance with an embodiment of the present invention, a mass spectrometry subsystem is utilized for analysis, and "spectral similarity" refers to a range of compounds in parent molecule of M+10 and its associated fragments, as reflected in its associate fragments. Focusing agents make use of this phenomenon and the appropriate choice should be based on compounds that behave similarly with regard to the fragmentation. A couple of examples follow:

Sarin is an organophosphorus compound with the formula $(CH_3)_2CHO_3CH_3P(O)F$. Sarin (or "GB") is a colorless, odorless liquid, used as a chemical weapon owing to its extreme potency as a nerve agent. It can be lethal even at very low concentrations, where death can occur within one to ten minutes after direct inhalation of a lethal dose, due to suffocation from lung muscle paralysis, unless some antidotes, typically atropine and an oxime, such as pralidoxime, are quickly administered. It is generally considered a weapon of mass destruction. Production and stockpiling of sarin was outlawed as of April 1997 by the Chemical Weapons Convention of 1993, and it is classified as a Schedule 1 substance. In June 1994, the UN Special Commission on Iraqi disarmament destroyed the nerve agent sarin under Security Council resolution 687 (1991) concerning the disposal of Iraq's weapons of mass destruction. Accordingly, sarin is an exemplary chemical agent that may be detected and quantified in accordance with embodiments of the present invention.

Diisopropyl fluoro phosphate (DIFP, a non-schedule 1 compound) bears a close relationship to sarin (GB), varying structurally by the replacement of the methyl group in sarin with an isopropoxy group, and can be used as an embedded standard to normalize the data to a previously established curve on a separate instrument. This would work by creating a calibration curve of sarin and DIFB on the same instrument (i.e., instrument 1). Field measurements with instrument 2 would have an analytical sampling device 14 embedded with a known quantity of DIFP and testing a sample having an unknown concentration or quantity of sarin. The concentration can then be determined by correlation. Another similar correlation can be drawn between mustard gas (HD) and 2-chloroethyl ethyl sulfide (CEES).

Figure 3:
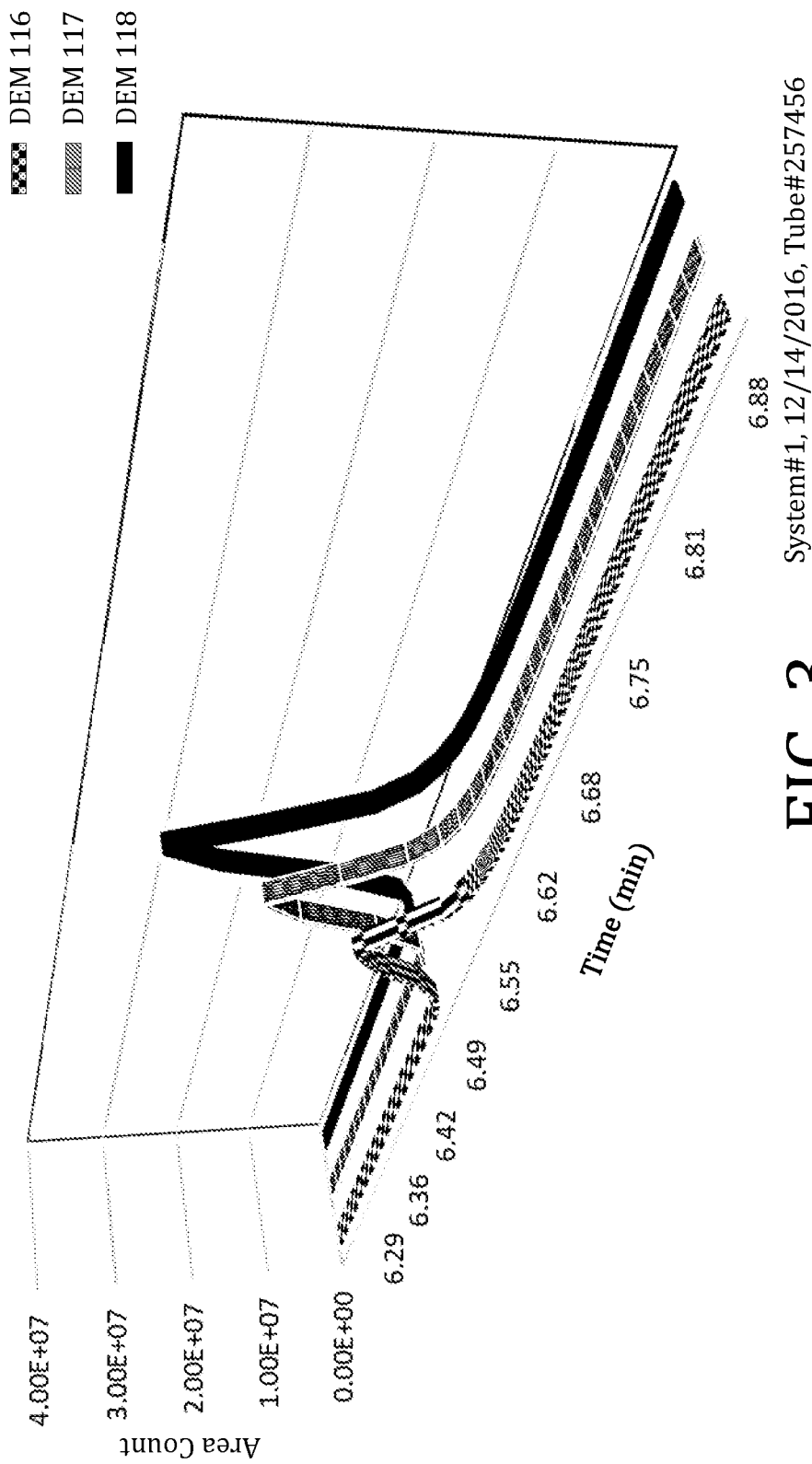
FIG. 3 is a three-dimensional plot of data showing a three-point curve of an analytical sampling device embedded with a focusing agent comprising three C-13 isotope analogs of diethyl malonate, where the data was obtained with a system and method in accordance with embodiments of the present invention.
Figure 4:
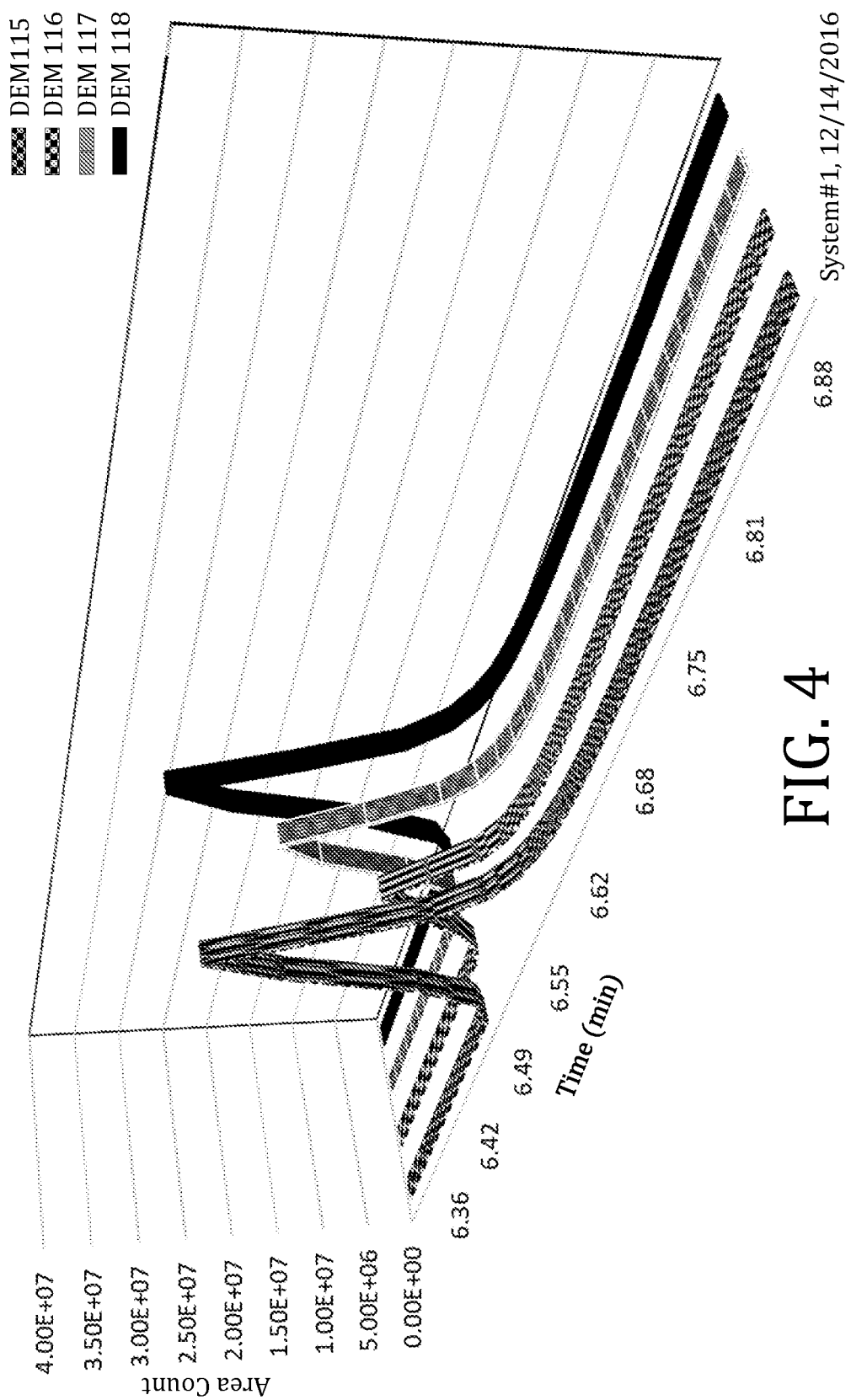
FIG. 4 is a three-dimensional plot of data of a three-point curve of an analytical sampling device applied with test sample of diethyl malonate, where the analytical sampling devices was previously embedded with a focusing agent comprising three C-13 isotope analogs of diethyl malonate, where the data was obtained with a system and method in accordance with embodiments of the present invention.

Finally, the method can be enhanced by using isotopic analogs of the target compounds or the focusing agent. Since mass spectral data can separate isotopic analogues, no previous calibration is required and each collected tube has a calibration embedded for analysis. As an example, diethyl malonate (MW 160) was selected as a model chemical agent. Exemplary isotopic analogs include diethyl malonate-2-$^{13}$C, diethyl malonate-1,2-$^{13}$C, or diethyl malonate-1,2,3-$^{13}$C, having MW 161, 162 and 163, respectively, and whose m/z ions for quantification can be 116, 117 and 118, respectively, as shown in FIGS. 3 and 4. Using the distinct masses for the isotopic analogs can achieve a linear curve.

Figure 5:
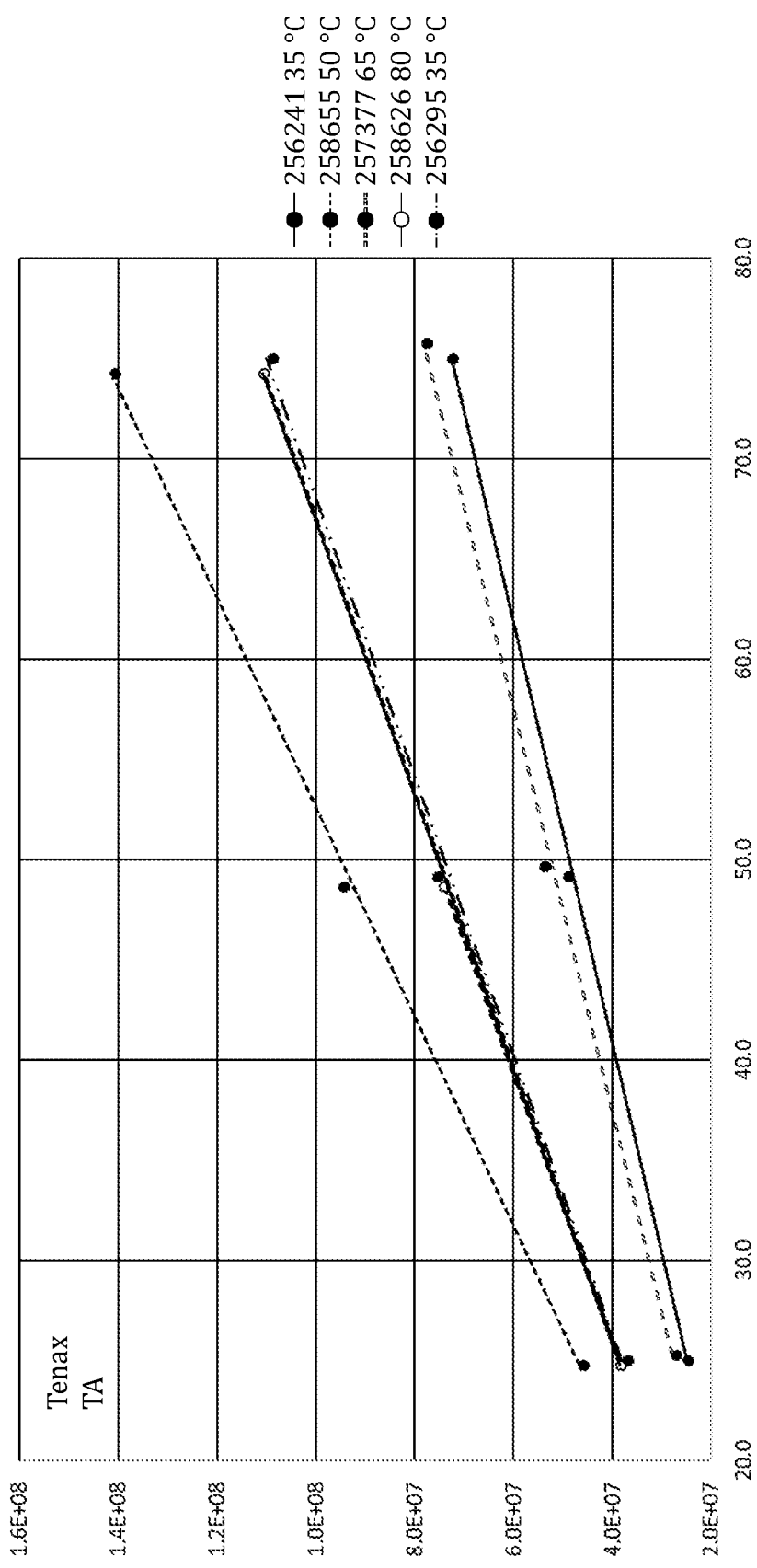
FIG. 5 is a linear plot of the focusing agent comprising three C-13 isotope analogs of diethyl malonate, where analysis was performed on three instruments over three months in triplicate to demonstrate the linearity, reproducibility, and stability of the system of the embodiments of the present invention.
Figure 6:
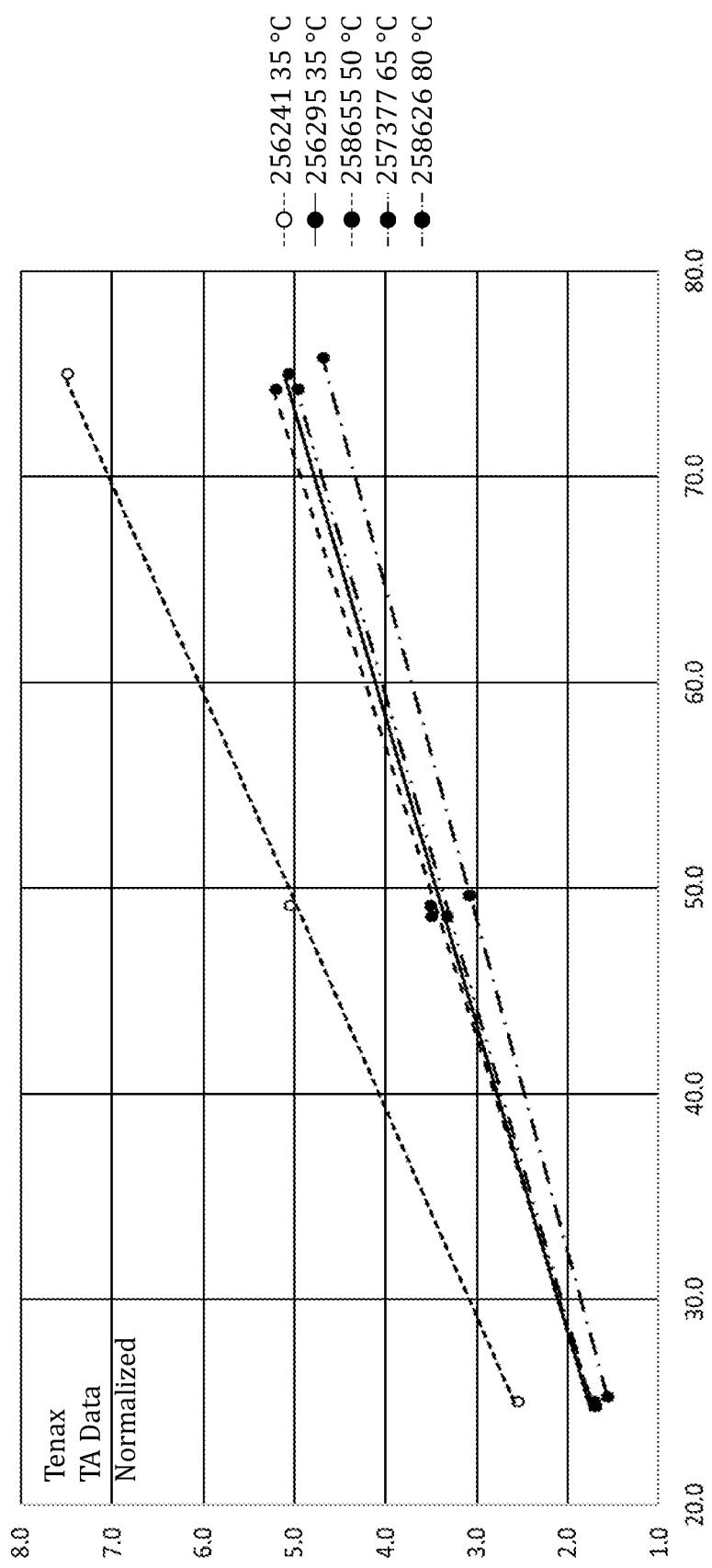
FIG. 6 is a linear plot showing the normalized data shown in FIG. 5.
Figure 7:
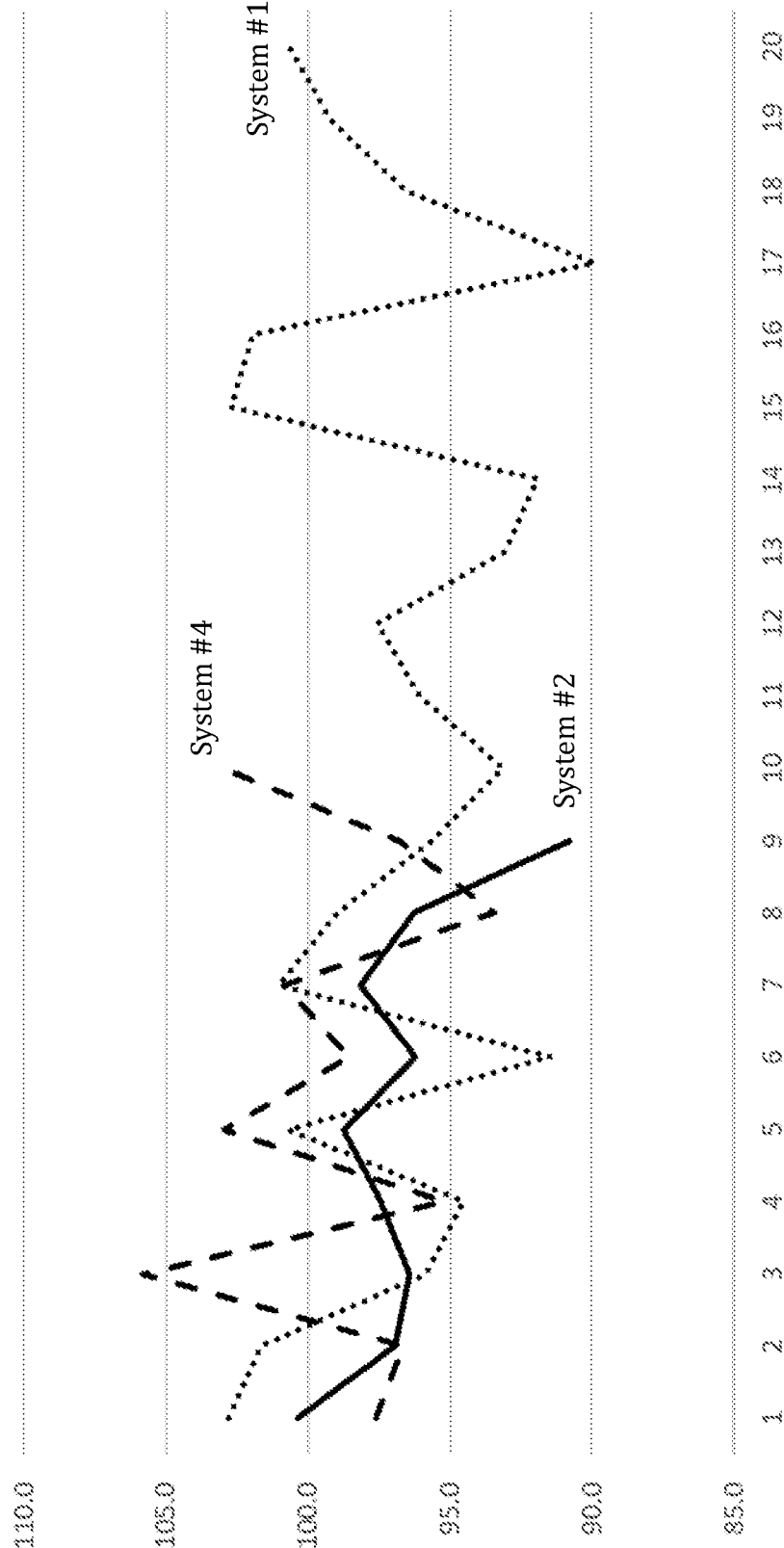
FIG. 7 is line plot showing percent recoveries of the embedded focusing agents comprising three C-13 isotope analogs of diethyl malonate.

These in-situ embedded tubes can then be used to collect the native diethyl malonate (MW 160) with a m/z ion at 115, as shown in FIG. 4. In this manner a three-point curve can be embedded yielding $r^2$ values of 1.0000±0.0015 yielding RSDs of ≤5%, as shown in FIGS. 5 and 6. In this manner field equipment can achieve results equal to or surpassing fix-based laboratory data. This technique can also be used as a diagnostic tool for the on-going examination of laboratory equipment. Quantitation has yielded remarkable recoveries at 100±5% (see FIG. 7).

The current work was based on the field detection and quantitation of Chemical Warfare Agents (CWA), thus, the FA were simulants that have previously been used in CWA work. It is our belief that the simulants which are semi-volatiles will have universality for other semi-volatiles that exhibit similar chromatographic similarities. Other FAs will be chosen dependent on the chemistry and chromatography of the chemicals of concern. Table 1 shows exemplary CWA surrogates/simulants and an exemplary focusing agent (bromopentafluorobenzene) applicable to same.

TABLE 1

Exemplary focusing agents, simulants, and surrogates for various chemical agents using a GC/MS technique.

| ION | RT[a] | Focusing agent | Chemical Agent |
|---|---|---|---|
| 117 | 3.37 | Bromopentafluorobenzene | |
| 75 | 4.45 | 2-Chloroethyl Ethyl Sulfide | Bis(2-chloroethyl)sulfide (HD) |
| 127 | 5.15 | Diisopropyl Fluoro Phosphate | Sarin (GB) |
| 79/97/125 | 5.59 | Diethyl Methyl Phosphonate | Sarin (GB) |
| 115 | 6.33 | Diethyl Malonate | General |
| 120 | 7.35 | Methyl Salicylate | General |
| 226/191 | 8.16 | Dichlorvos-d6 | general |
| 220/205 | 12.59 | Atrazine-d5 | Pyrethroids |

[a]All chemicals were chromatographically identified using the HAPSITE ER on the CWA profile as supplied. Atrazine-d5 was used as an internal standard for the analysis of transflutherin (unpublished). The pyrethroid analyses were conducted on a Thermo-Fisher TSQ mass GCMS. The method used was the commercially available method provided by Inficon for CWA analysis.

A process for incorporating focusing agents onto the adsorbent media of the analytical sampling device is also provided. The focusing agents were injected as solutions in an organic solvent, such as acetonitrile, onto the thermal desorption tubes using a commercial Calibration Solution Loading Rig (CLSR™) from Markes International, Inc, Cincinnati, Ohio at 20 psi at approximately 60 mL/min. The tubes, once loaded, were then dry conditioned at 50° C., 50-60 mL $N_2$ flow, at 20 psi for 1.5 hours using a Markes TC-20 (from Markes International, Inc, Cincinnati). The prepared tubes were then stored at room temperature and the analyses were conducted over a period of one month at a minimum of three points.

Studies were performed to investigate the effect of loading temperature on the embedding process and stability of focusing agents on the analytical sampling device (e.g., a thermal desorption tube). The embedding experiments were conducted at about 35° C., about 50° C., about 65° C., about 80° C., and about 95° C. Thus, in accordance with an embodiment of the present invention, a focusing agent may be embedded into the analytical sampling device at a temperature in a range from about 35° C. to about 95° C. For example, the embedding temperature may be about 35° C., about 40° C., about 45° C., about 50° C., about 55° C., about 60° C., about 65° C., about 70° C., about 75° C., about 80° C., about 85° C., about 90° C., about 95° C., or in a range between any two of the foregoing. In another embodiment, the embedding temperature may be in a range from about 50° C. to about 65° C., with stability to about 95° C. Excellent recoveries were observed at all temperatures but suppression was observed at an embedding temperature of about 35° C., which may indicate that the acetonitrile used as solvent may not be completely removed.

Initial trials were done at a constant concentration of the focusing agent. Subsequent experiments were conducted by preparing the analytical sampling device under similar conditions, but at four concentration levels. Stability was measured over a period of one month. The conditions chosen represented the highest field temperature conditions expected. The concentrations were chosen based on the response of the focusing agent over a minimum of three instruments. Current experiments have demonstrated reduction of variability as measured by relative standard deviation (RSD) from 70% to less than 20%, where the industry standard is generally <30% RSD.

When the procedure for adsorbing the exemplary focusing agents onto a Tenax® TA resin is followed, the focusing agent has been shown to be stable for over 1 month or more (e.g., 2 months or 3 months or more) at room temperature. Further stability testing approximated harsh sampling conditions and, again, the focusing agent on the media was stable at 60 mL/min at 50° C. for 1.5 hours. The process has demonstrated the viability of the addition of a focusing agent, sampling under elevated temperatures. Under analytical conditions for thermal desorption, the focusing agents were released and virtually quantitative recoveries were observed. Tubes prepared in this manner are expected to be used under a variety of field conditions and/or for samples returned to the laboratory. Since it adds a known substance at a prescribed concentration, it will also assist with determining quantities for unknown compounds that were not calibrated for.

The Focusing Agents that track sampling from field collection to laboratory/field analysis could be applied to a variety of media packed in a multitude of configurations (tubes, dosimeters, impingers, etc.). The technique could be used across a variety of analytical applications and is not just limited to gas chromatography mass spectrometry. It is immediately applicable to liquid chromatography (LC) mass spectrometry and other LC techniques with some modification. Other analytical techniques may also benefit, but additional work on selection of FA would be required.

While the present invention was illustrated by the description of one or more embodiments thereof, and while embodiments have been described in considerable detail, they are not intended to restrict or in any way limit the scope of the appended claims to such detail. For example, incorporating focusing agents into other sampling devices for other analytical techniques is envisioned. Additional advantages and modification will readily appear to those skilled in the art. The invention in its broader aspects is therefore not limited to the specific details, representative product and method, and illustrative examples shown and described. Accordingly, departures may be made from such details without departing from the scope of the general inventive concept embraced by the following claims.

What is claimed is:

1. A method for reducing a relative standard deviation (RSD) in an analytical chromatographical testing procedure for quantifying a chemical agent, comprising:
   obtaining an analysis sample with an analytical sampling device, the analytical sampling device having an adsorbent material therein onto which the analysis sample is adsorbed, the adsorbent material having a focusing agent adsorbed therein, wherein the focusing agent including a plurality of isotope analogs of the chemical agent with each isotope analog of the plurality being at a concentration that is different from concentrations of other isotope analogs of the plurality;
   desorbing the focusing agent and the analysis sample from the analytical sampling device to form a desorbed mixture and transferring the desorbed mixture a chromatographical system;
   observing a first signal relating to the focusing agent and a second signal relating to the chemical agent; and
   correcting the second signal with the first signal wherein an RSD of the corrected second signal is reduced compared to an RSD resulting from a use of an internal standard or an existing calibration curve.

2. The method of claim 1, wherein desorbing the focusing agent and the chemical agent from the analytical sampling device further comprises:

adsorbing the desorbed mixture onto a second pre-concentrator operably connected to the chromatographic system; and performing a second desorption process from the second pre-concentrator prior to transferring the desorbed mixture into the chromatographic system.

3. The method of claim 1, wherein the focusing agent comprises a semi-volatile compound.

4. The method of claim 3, wherein the semi-volatile compound is selected from the group consisting of bromopentafluorobenzene, diisopropyl fluoro phosphate, a dialkyl malonate, or a combination thereof.

5. The method of claim 3, wherein the semi-volatile compound is a dialkyl malonate selected from dimethyl malonate, diethyl malonate, dipropyl malonate, diisopropyl malonate, dibutyl malonate, dipentyl malonate, or a combination thereof.

6. The method of claim 5, wherein dialkyl malonate comprises diethyl malonate, and optionally comprises an isotopic derivative selected from diethyl malonate-2-$^{13}$C, diethyl malonate-1,2-$^{13}$C, or diethyl malonate-1,2,3-$^{13}$C.

7. The method of claim 1, wherein the adsorbent material comprises alumina, silica, carbon-containing adsorbents, a zeolite, a porous glass, a clay, a porous polymer based on 2,6-diphenyl-p-phenylene oxide, a hydrophobic copolymer of styrene-divinylbenzene resin, a polyurethane, or a combination thereof.

8. The method of claim 1, wherein a relative concentration of the isotope analogs of the plurality is 1:2:3.

9. The method of claim 1, wherein the isotope analogs of the plurality are 13C isotope analogs of diethyl malonate.

* * * * *